United States Patent
Shan et al.

(10) Patent No.: US 7,801,592 B2
(45) Date of Patent: Sep. 21, 2010

(54) HEART RATE VARIABILITY AS PREDICTOR OF POSTOPERATIVE NAUSEA AND VOMITING

(76) Inventors: William Li Pi Shan, 1515 Dr. Penfield Avenue, Apt. 406, Montreal, QC (CA) H3G 2R8; Roupen Hatzakorzian, 3600 Park Avenue, Apt. 702, Montreal, QC (CA) H2X 3R2; Pierre Fiset, 36 Avenue du Mont St-Bruno, Ste-Julie, QC (CA) J3E 2Z9; Alain Deschamps, 2500 Chemin Côte Ste-Catherine, Montreal, QC (CA) H3T 1B2

( * ) Notice: Subject to any disclaimer, the term of this patent is extended or adjusted under 35 U.S.C. 154(b) by 549 days.

(21) Appl. No.: 11/763,722

(22) Filed: Jun. 15, 2007

(65) Prior Publication Data
US 2007/0293777 A1  Dec. 20, 2007

Related U.S. Application Data

(60) Provisional application No. 60/804,881, filed on Jun. 15, 2006.

(51) Int. Cl.
*A61B 5/0402* (2006.01)
*A61B 5/0245* (2006.01)

(52) U.S. Cl. .................. 600/509; 600/508; 600/519

(58) Field of Classification Search ............... 600/508, 600/509, 519
See application file for complete search history.

(56) References Cited

U.S. PATENT DOCUMENTS

2006/0080150 A1 * 4/2006 Patterson et al. ............... 705/3

OTHER PUBLICATIONS

Akselrod et al. "Power spectrum analysis of heart rate fluctuation: a quantitative probe of beat-to-beat cardiovascular control" Science. 1981; 213:220-222.
Apfel et al. "A risk score to predict the probability of postoperative vomiting in adults" Acta anaesthesiol scand 1998; 42: 495-501.
Ashraf et al. "Evidence-based management of postopertive nausea and vomiting: a review" Can J Anesth 2004; 51:326-341.
Bellville et al. "Postoperative nausea and vomiting. IV. Factors related to postoperative nausea and vomiting." Anesthesiology 1960: 186-193.
Bigger et al. "Frequency domain measures of heart period variability and mortality after myocardial infarction." Circulation. 1992; 85:164-171.
Task Force of the European Society of Cardiology the North American Society of Pacing Electrophysiology "Standards of Measurement, Physiological Interpretation, and Clinical Use" Circulation 1996; 93: 1043-1065.
Cohen et al. Anesth Analg 1994; 78:7-16.
Deschamps et al. "Autonomic Nervous System Response to Epidural Analgesia in Laboring Patients by Wavelet Transform of Heart Rate and Blood Pressure Variability" Anesthesiology 2004; 101: 21-27.

(Continued)

*Primary Examiner*—Carl H Layno
*Assistant Examiner*—Yun Haeng Lee
(74) *Attorney, Agent, or Firm*—Bereskin & Parr LLP/S.E.N.C.R.L., s.r.l.

(57) ABSTRACT

The invention relates to methods and systems to predict postoperative nausea and vomiting (PONV).

11 Claims, 2 Drawing Sheets

OTHER PUBLICATIONS

Gianaros et al "Relationship between temporal changes in cardiac parasympathetic activity and motion sickness severity" Psychophysiology 2003; 40(1):39-44.

Gold et al. "Unanticipated admission to the hospital following ambulatory surgery" JAMA 1989; 262:3008-10.

Hon et al. "Electronic evaluations of the fetal heart rate patterns preceding fetal death: further observations" Am J Obstet Gynecol. 1965; 87: 814-826.

Kawase et al. "Heart Rate Variability and Arterial Blood Pressure Variability Show Different Characteristic Changes During Hemorrhage in Isoflurane-Anesthetized, Mechanically Ventilated Dogs" Anesthesia and Analgesia 2002; 94: 16-21.

Kleiger et al. "Decreased heart rate variability and its association with increased mortality after acute myocardial infarction" Am J Cardiol. 1987; 59: 256-263.

Koivuranta et al "A survey of postoperative nausea and vomiting" Anaesthesia 1997; 52: 443-449.

Kranke et al. "The Efficacy and Safety of Transdermal Scopolamine for the Prevention of Postoperative Nausea and Vomiting: A Quantitative Systematic Review" Anesth Analg 2002; 95:133-43.

Lerman "Surgical and patient factors involved in postoperative nausea and vomiting." Br J Anaesth 1992; 69:40S-45S.

Maier et al. Clinical Science 1996; 91: 67.

Morrow "Vagal changes following cancer chemotherapy: Implications for the development of nausea" Psychophysiology 2000; 37(3): 378-84.

Flapan et al. "Effect of captopril on cardiac parasympathetic activity in chronic cardiac failure secondary to coronary artery disease." Am J Cardiol. 1992; 69:532-535.

Pichot et al. "Wavelet transform to quantify heart rate variability and to assess its instantaneous changes" Journal of Applied Physiology 1999; 86: 1081-1091.

Pomeranz et al. "Assessment of autonomic function in humans by heart rate spectral analysis." American Journal of Physiology 248: H151-153, 1985.

Sayers "Analysis of heart rate variability (Blood pressure and body temperature dynamic control systems and respiration relationship to heart rate variability)" Ergonomics 1973; 16: 17-32, Task Force of the European Society of Cardiology and the North American Society of Pacing and Electrophysiologyecol. 1965; 87: 814-826.

Sleigh et al. "Comparison of bispectral index, 95% spectral edge frequency and approximate entropy of the EEG, with changes in heart rate variability during induction of general anaesthesia" BJA 1999; 82: 666-671.

Stern "The psychophysiology of nausea" Acta Biologica Hungarica. 2002; 53(4): 589-99.

Voss et al. "The application of methods of non-linear dynamics for the improved and predictive recognition of patients threatened by sudden cardiac death." Cardiovasc Res. 1996 31(3):419-33.

Watcha, "Postoperative nausea and emesis." Anesthesiol Clin North America. 2002, 20(3):709-722.

* cited by examiner

HEART RATE VARIABILITY AS PREDICTOR OF POSTOPERATIVE NAUSEA AND VOMITING

FIELD OF THE INVENTION

The invention relates to methods and systems to predict postoperative nausea and vomiting (PONV).

BACKGROUND OF THE INVENTION

Postoperative nausea and vomiting (PONV) is one of the most common complaints in the postoperative period. It causes significant distress to patients after surgery. Despite all the advances in the last decades, the incidence of PONV is still between 20-30% (Cohen et al. Anesth Analg 1994; 78:7-16, Watcha, Anesthesiology Clin. N Am 2002; 20:709-722). Many different factors are associated with PONV; such as a past history of PONV, female gender, gynecological surgery, long duration of surgery, volatile anesthetics, postoperative opioids (Lerman Br J Anaesth 1992; 69:40S-45S), history of non-smoking and motion sickness (Ashraf et al. Can J Anesth 2004; 51:326-341). PONV also causes an increase in health care cost by prolonging stay in hospital (Gold et al. JAMA1989; 262:3008-10). There are many pharmaceutical options that have been developed over the past decades to treat PONV such as ondansetron, metoclopramide, propofol, corticosteroids and anticholinergics. Universal prophylaxis against PONV is neither cost-effective nor necessary. The best cost effective approach to manage PONV is to predict beforehand which patients will have nausea and vomiting after the surgery and to prevent its occurrence. There are ways to predict PONV by developing risk scores based on the before mentioned risk factors (Bellville et al. Anesthesiology 1960: 186-193). But there is currently no effective way to anticipate PONV. Female gender has been associated with a higher incidence of PONV compared to male patients (Koivuranta et al Anaesthesia 1997; 52: 443-449, Apfel et al. Acta anaesthesiol scand 1998; 42: 495-501). Gynecological surgery is a good setting to analyze PONV because patients are exclusively female; thus a higher incidence of PONV. Nausea is dependent on inherent factors such as age, gender and race and psychological factors such as anxiety, expectation and anticipation (Stern Acta Biologica Hungarica. 2002; 53(4): 589-99). The autonomic nervous system is implicated in the physiology of nausea. Increases in sympathetic activity and decreases in parasympathetic activity occur during nausea with an increase in abnormal dysrhythmic gastric activity and an increase in plasma vasopressin (Gianaros et al Psychophysiology 2003; 40(1):39-44). This can be seen in motion sickness and chemotherapy-induced nausea. It has also been also noted that an increase in baseline parasympathetic activity seems to set the stage for the expression of nausea (Morrow Psychophysiology 2000; 37(3): 378-84). Knowing that the autonomic system is implicated in the physiology of nausea, anticholinergic medications like scopolamine, which blocks muscarinic cholinergic central nervous system emetic receptors in the cerebral cortex and pons, have been used to treat PONV successfully (Kranke et al. Anesth Analg 2002; 95:133-43).

SUMMARY OF THE INVENTION

In one embodiment of the invention there is provided a method for determining whether an individual is at risk for post operative nausea and vomiting PONV, said method comprising a) measuring a parameter of the autonomous nervous system of said individual preoperatively; and
b) deriving a predictive value of risk of PONV based on said measured parameter.

The autonomic system parameter may be selected from parasympathetic and sympathetic tone.

The parameter may be obtained from an ECG of said individual.

The parameter may be a heart rate variability (HRV) measurement.

The HRV measurement may be based on a frequency of a component of said ECG.

The parameter may be a parasympathetic tone and the frequency may be a high frequency.

The parameter may be sympathetic tone and the frequency may be a low frequency.

The frequency may be obtained by wavelet transform to generate a wavelet coefficient.

The component may be selected from R signal, P signal, S signal and T signal.

The component may be R signal.

There is also provided a method for treating PONV in an individual said method comprising a) determining if said individual is at risk for PONV; and
b) administering an anti-emetic to said individual.

In an other aspect of the invention there is provided a system for determining whether an individual is at risk for PONV comprising a) electrocardiogram measuring (ECG) means
b) ECG processor for deriving HRV measurements
c) HRV data processor to determine a coefficient related to risk of PONV; and
d) an acquisition control/user feedback module.

The HRV data processor may comprise means for calculating wavelet transform coefficient.

The system may further comprise comparator means for comparing said wavelet transform coefficient with predetermined values of wavelet transform coefficient wherein the comparison determines whether said individual is at risk of PONV.

BRIEF DESCRIPTION OF THE DRAWINGS

Further features and advantages of the present invention will become apparent from the following detailed description, taken in combination with the appended drawings, in which.

DETAILED DESCRIPTION OF THE INVENTION

Heart rate has been traditionally employed to measure the autonomic nervous system. Heart rate variability (HRV) is a sensitive tool to measure the autonomic drive. HRV was first introduced in 1965 by Han and Lee to assess the variability in fetal heart rate (Hon et al. Am J Obstet Gynecol. 1965; 87: 814-826). In 1981, Akselrod et al. studied power spectral analysis of heart rate fluctuations to quantitatively evaluate beat to beat cardiovascular control (Akselrod et al. Science. 1981; 213:220-222). HRV has been found to be a strong and independent predictor of mortality after acute myocardial infarction (Kleiger et al. Am J Cardiol. 1987; 59: 256-263, Bigger et al. Circulation. 1992; 85:164-171). Heart rate variability represents the variation in the output of the parasympathetic and sympathetic systems to the sinoatrial node. The parasympathetic nervous system mediates HRV through the high frequency regions of the power spectrum, while the low frequency power spectrum can be considered a combination of both parasympathetic and sympathetic drives (Pomeranz et al. American Journal of Physiology 248: H151-153, 1985). Spectral analysis of HRV has been used in various clinical settings. A decrease in high frequency power spectrum (parasympathetic activity) is associated with cardiac failure (Nolan et al. Am J Cardiol. 1992; 69:482-485), with high risk patients following myocardial infarction (Voss et al. Clinical Science 1996; 91: 118-119) and with increased risk of arrhythmia in patients with coronary artery disease (Maier et al. Clinical Science 1996; 91: 67). Heart rate variability has also been used to analyze the autonomic nervous system during anesthesia (Sleigh et al. BJA 1999; 82: 666-671, Kawase et al. Anesthesia and Analgesia 2002; 94: 16-21).

Figure 1:
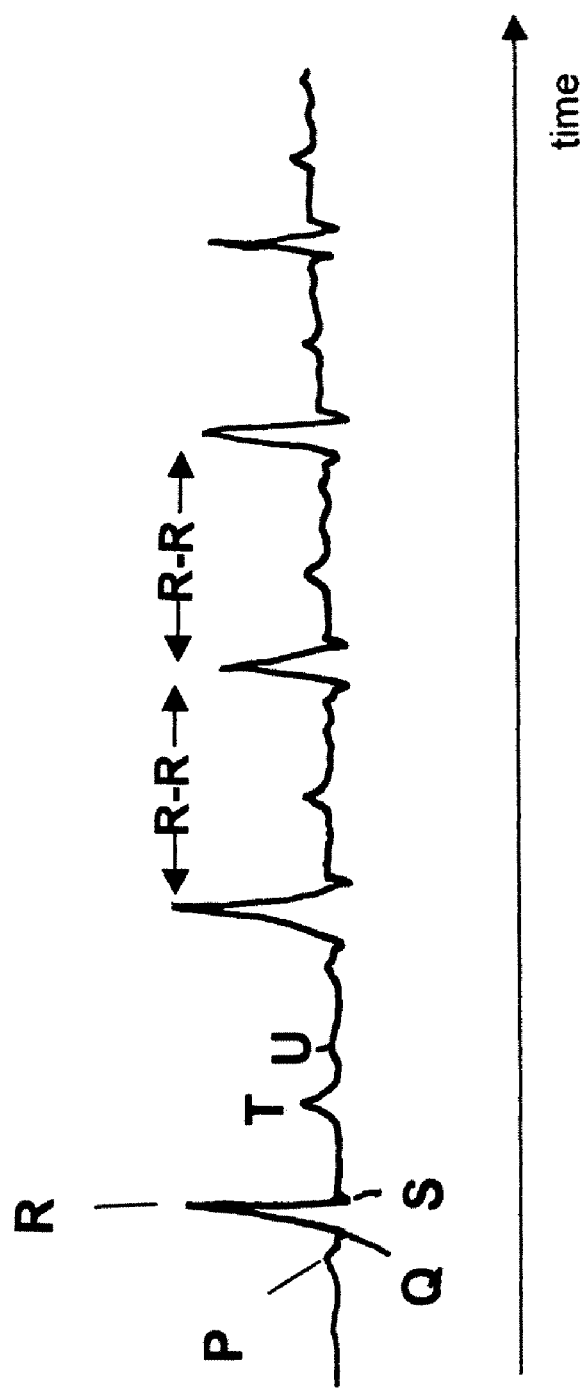
FIG. 1 is a ECG trace showing the characteristic parts of the signal.
Figure 2:
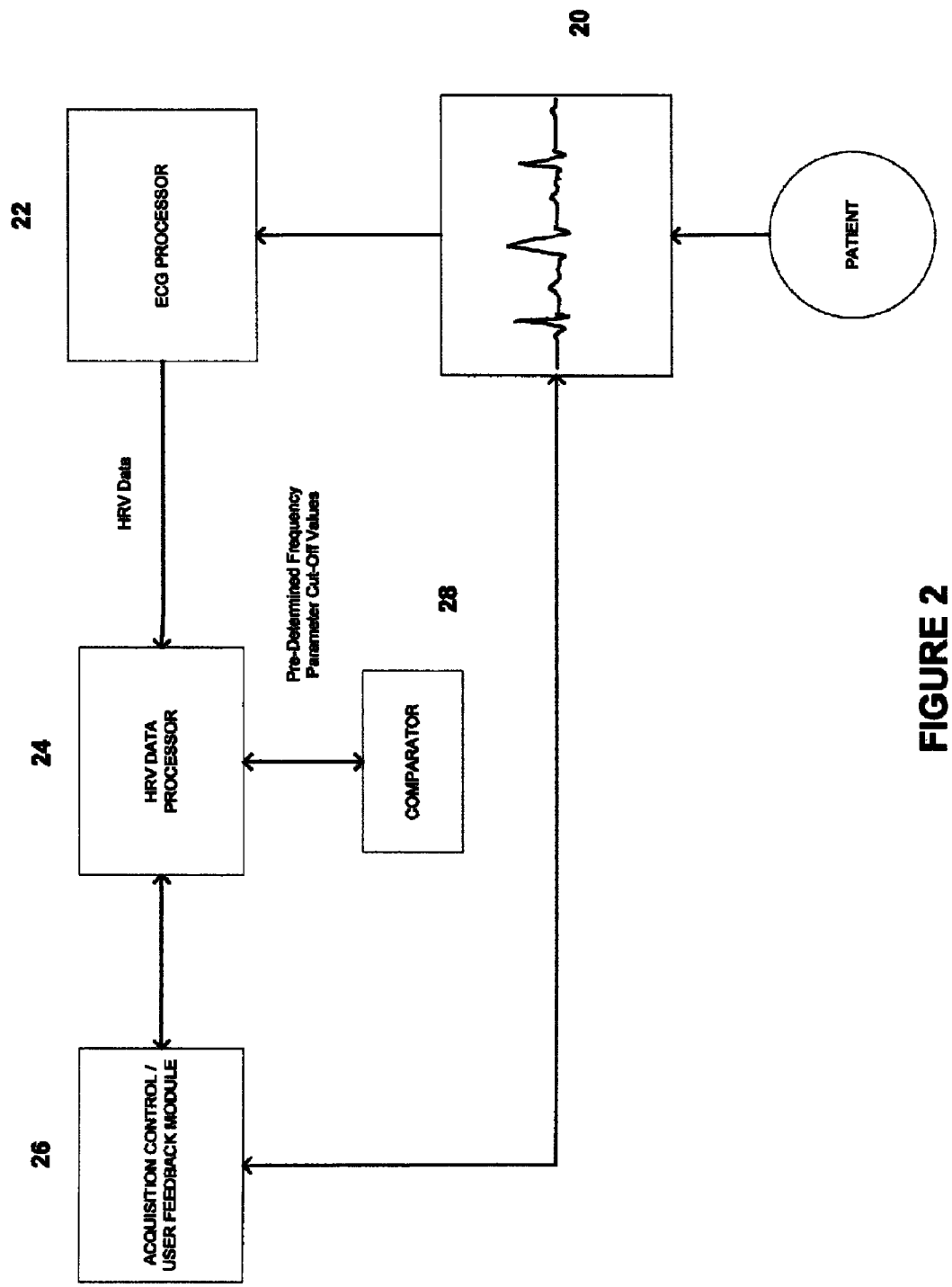
FIG. 2 is a schematic diagram of an embodiment of the system of the invention.

In one embodiment there is provided a method for determining a risk or propensity of an individual to develop postoperative nausea and vomiting (PONV). The method comprises measuring a parameter of autonomic nervous system in the individual. In a preferred embodiment the parameter is a measurement of parasympathetic and/or sympathetic tone that can be derived from HRV based on an ECG signal of the individual. Characteristic features of ECGs are well known in the art and include the P, Q, R, S, T and U waves. Heart rate variability can be estimated by measuring the variations in the frequency of one of the characteristic part of the ECG. For example, the period between several R signals can be measured to characterize the HRV (see FIG. 1). In a preferred embodiment the frequency of a particular signal of the ECG is obtained by a transform and preferably by a wavelet transform. The ECG may be acquired for several minutes and preferably for at least 10 minutes and more preferably for at least 20 minutes. The time of acquisition should be sufficient to obtain enough data to derive a parameter that correlates with PONV.

The use of wavelet transform to perform a spectral analysis of HRV has been described (Sayers, Ergonomics 1973; 16: 17-32, Task Force of the European Society of Cardiology and the North American Society of Pacing and Electrophysiology. Circulation 1996; 93: 1043-1065, Pichot et al. Journal of Applied Physiology 1999; 86: 1081-1091). Deschamps et al. have used this method successfully to show an increase in parasympathetic tone and a decrease in sympathetic tone with epidural analgesia in laboring patients (Deschamps et al. Anesthesiology 2004; 101: 21-27).

From the wavelet transform, standard indices of the autonomic system can be calculated. Typically, the ECG characteristic signals are dynamic and non-stationary i.e. Consecutive R-R intervals change with respect to time and are rarely constant. Thus in a preferred embodiment, wavelet transform analysis of HRV is used to analyze dynamic signals because it allows a temporally localized sliding analysis of the signal while the signal is changing in time when the balance of the autonomic nervous system is suddenly modified. Also the shape of the wavelet transform-analyzing equation can fit the shape of the analyzed signal, allowing a good quantitative measurement.

Spectral analysis of HRV using wavelet transform can be accomplished as described in details by Pichot et al. (supra). This analysis is devoted to the extraction of characteristic frequencies, or specific oscillations, of a signal that is composed of the consecutive R-R intervals for HRV analysis. Wavelet transform is usually devoted to the analysis of non-stationary signals and thus there is no prerequisite over the stability of the frequency content over the signal analyzed.

Wavelet analysis allows one to follow the temporal evolution of the spectrum of the frequencies contained in the signal. The continuous wavelet transform is an integral transform. The decomposition of a signal by wavelet transform requires a mathematical function adequately regular and localized, called the "Mother Wavelet Function". Starting from this initial function, a family of functions is built by dilatation and translocation of the mother wavelet function, which constitute the so-called "wavelet frame" or levels. Wavelet analysis can be considered as a local fast Fourier transform analysis performed at different separated levels. The analysis amounts to sliding a window of different weights (corresponding to different levels) containing the wavelet function along the signal. The weight characterizes a family member with a particular dilatation factor. Serial lists of coefficients called "wavelet coefficients" are obtained which represent the evolution of the correlation between the signal and the chosen wavelet at different levels of analysis (or different ranges of frequencies) all along the signal. The smallest scaled wavelet compares the length of two ($2^1$) consecutive R-Rs giving the highest frequency analyzed. The level immediately above compares the length of four ($2^2$) consecutive RRs, and thus compares half as much length of the signal, and the frequency analyzed is halved compared to the previous level. Therefore the maximum number of points that can be analyzed is limited to the last complete $2^n$ set of R-Rs that can be extracted from the whole data set. In this study, the maximum number of increments was chosen to be 5 levels ($2^5$) or 32 consecutive R-R intervals. The Daubechies 4 wavelet transform was chosen. The variability power is calculated as the sum of squares of the coefficients for each level for a given time interval, 2 minutes in the present study. The mathematical analysis can be made for example using MATLAB and the dedicated toolbox software Wavelab. Levels 2, 4, 8 correspond to the high frequency power level (0.15-0.4 Hz) in the FFT analysis, with the frequency diminishing by half at every consecutive level. Levels 16 and 32 correspond to the low frequency power level (0.04-0.15 Hz) in the FFT analysis.

To establish a threshold value, a correlation coefficient can be obtained between baseline parasympathetic and/or sympathetic tone and occurrence of PONV. Based on the strength of this coefficient the sensitivity, specificity, positive and negative predictive value can be calculated and a plot of the receiver operating curve obtained to determine the accuracy of our clinical test.

In another aspect of the invention there is provided a system for measuring the risk of an individual to develop PONV. The system comprises an ECG 20 measuring means, an ECG processor 22 for analysing the ECG so as to obtain HRV measurements based on characteristic signal from the ECG, an HRV measurements processor 24 to calculate a frequency parameter (such as a wavelet coefficient) of the characteristic signals of the ECG and an acquisition control/user feedback module 26 to provide feedback and results to the user. The frequency parameters generated at processor 24 can be compared with a predetermined cut-off value at comparator 28 which allows the establishment of a PONV prediction. The PONV prediction, associated statistics, ECG parameters and the like can be provided to the user at module 26. It will be appreciated that the appropriate feedback signal can be provided to the user to indicate whether the patient is at risk of PONV. The signal may be visual such as a written message/numbers on a display or can also be an audible signal. Also the acquisition control/user feedback module 26 can be used to modify the ECG acquisition parameters such as time of acquisition and the like.

As described above, transform methods to derive frequency data such as wavelet transform are well known in the art and software to effect calculations are readily available. Thus the HRV measurements processor 24 may comprise such software.

Continuous recording of heartbeats can be obtained with a three lead electrocardiogram (ADInstruments, mountain View, Calif., USA). Electrocardiogram signals can be collected via an analogue-to-digital converter at a sampling rate of one KHz per channel (Powerlab, ADInstruments, Mountain View, Calif., USA) and saved on a computer such as a portable computer. The digital signals are then analyzed using existing software Matlab). The signals are then converted using the wavelet transform technique until wavelet coefficients are obtained from the raw data. The wavelet coefficient is a single number that is an approximation of the power of heart rate variability.

It will be appreciated that all the components of the system can be incorporated into a portable unit, allowing measurements and calculation to be made at bedside and providing real time results to the user.

Example 1

Materials and Methods

Following REB approval and patient consent, ECG and non-invasive continuous blood pressure measurement were obtained preoperatively in 20 women undergoing abdominal hysterectomy. Wavelet transform was used for analysis of HRV and BPV. Five wavelet coefficients were calculated ($2^1$ to $2^5$) for HRV and BPV. Lower coefficients correspond to high frequency power and higher coefficients to low frequency power. All patients received a standard anesthetic. Anti-emetic prophylaxis and neuraxial techniques were avoided. PONV was assessed for 24 hrs following surgery.

Results

Table 1 displays the results found with the nausea group (N=15) and the no nausea group (N=5), showing the difference in mean wavelet coefficients and their respective p-values (using Mann-Whitney test). Fifteen patients (75%) experienced PONV. Cumulative wavelet coefficients for 20 min were statistically analyzed using the Mann-Whitney test for non-parametric data.

TABLE 1

| | Mean Wavelet coefficient of Heart rate variability (SD) | | |
|---|---|---|---|
| | Nausea | No Nausea | P-value |
| HF | 113526.1 (119859) $sec^2$ | 43671.8 (52138) $sec^2$ | P < 0.0001 |
| Median | 64046 $sec^2$ | 22609 sec2 | P < 0.0001 |
| LF | 72887.5 (73847) $sec^2$ | 26418.8 (26001) $sec^2$ | P < 0.0001 |
| Median | 51437 $sec^2$ | 18939 $sec^2$ | P < 0.0001 |

Using the HF range of HRV, we found that the mean cumulative wavelet coefficient in the nausea group was significantly greater (p<0.0001) than the no nausea group. The LF range also showed a significant difference (p<0.0001) between the nausea group and the no nausea group. The HF range of HRV corresponds to predominant parasympathetic activity.

Discussion

Our preliminary results suggest an increased parasympathetic tone in patients with nausea and an increased sympathetic tone in patients without nausea. Using a non-invasive baseline measurement of HRV and BPV, it is possible to predict those patients at significant risk of developing PONV. Most validated regression models of PONV prediction use the receiver operating curve (ROC) as a measure of the predictive accuracy of their model. Most of the models in the literature are composed of a multiple regression model as a function of several variables which result in a probability of an event happening in this case PONV. The basic form of their models take the form $P=b0+b1x1+\ldots+bkxk$ whereby b are weighted coefficients and x are the risk factors. The model is then used in clinical trials to predict whether there is a good correlation or fit between the predicted incidence of PONV and the actual incidence. The area under an ROC (range 0-1) is a good index of how accurate the model fits real life. An area of 0.5 is the least accurate, 0.7-0.8 is fair, >0.8 is a good fit and >0.9 is excellent. Most models of PONV range from 0.6-0.7 which indicates a fair accuracy. These models have been tested in the field and have been validated on real patients. Usually the x variables include gender, prior history of PONV, non-smoking status and postoperative opioids. Our model contains only one variable, the high frequency wavelet coefficient. The are under the ROC yielded a result of 0.8 (95% CI 0.563-0.941, SE=0.104, P<0.0041) a good fit which is better than ever reported in the literature. Most reports utilize a multiple regression model with four known variables to predict PONV. These four variables include female gender, non-smoking status, history of PONV or motion sickness and use of postoperative opioids. These studies have been validated and their predictive values show an area under the ROC curve of 0.6-0.7. These are the most validated variables used to predict PONV but two variables, history of PONV and postoperative opioid use are not available for patients undergoing first time surgery. Our model takes into account only one variable, the wavelet transform coefficient taken immediately preoperatively which gives us all the information available to predict PONV.

Example 2

Materials and Methods

Subjects. With the approval of the institutional review board of the Royal Victoria Hospital (Montreal, Canada), informed written consent was obtained on the day of surgery from thirty-eight females (aged 26-61 years, ASA status I and II) undergoing gynecological surgery. The study was conducted from July 2005-September 2006. Exclusion criteria were: patient refusal, patients with ASA class 3 or above, patients on medications affecting heart rate (antiarrhythmics including beta blockers or agonists, calcium channel blockers, digoxin, muscarinic agonists or antagonists), patients with a cardiac rhythm other than sinus or with the presence of premature ventricular beats.

Data acquisition. Patient recruitment was performed preoperatively in the post anesthesia care unit (PACU) one to two hours before surgery. A preoperative interview was conducted for risk factors for PONV prior to data acquisition. Baseline vital signs were obtained in all patients followed by continuous electrocardiogram monitoring. Lead II (ADInstruments, Mountain View, Calif.) was monitored for a total of 20 min according to the task force recommendations with the patients supine and as stationary as possible. The electrocardiogram signal was converted from an analog to digital using a sampling rate of 1000 Hz/channel (PowerLab; ADInstruments) and then stored on a portable computer (PowerBook G4, Apple Inc., Cupertino, Calif.).

Study protocol. No premedication and no antiemetic prophylaxis was given prior to induction. After HRV data acquisition in the PACU, the patients were transferred to the OR, where an intravenous (IV) line and standard monitors were placed (3 lead EKG, blood pressure measurement, pulse oximetry). All patients then received a general anesthetic. Intravenous induction was performed with midazolam 10-30 µm/kg, propofol 2 mg/kg, rocuronium 0.5 mg/kg, fentanyl 1-2 µm/kg, followed by endotracheal intubation. Anesthesia was maintained with a 50%/50% air/oxygen mixture, sevoflurane 1 MAC and additional doses of fentanyl 0.5 µm/kg IV titrated to keep heart rate and systolic blood pressure within 20% of baseline. End tidal carbon dioxide tension was maintained between 30-40 mmHg with the appropriate ventilator adjustments. No anti-emetic medication was administered intraoperatively. A maximum of 20 ml/kg of normal saline (NS) was administered during the procedure to all patients. If there was no recovery to train-of-four stimulation, a neuromuscular reversal dose of neostigmine 35 µm/kg and 10 µm/kg of glycopyrrolate was given. At the end of the procedure, sevoflurane was discontinued and all patients were extubated in the OR and transferred to the PACU. In the PACU, vital signs and a ten point pain score were recorded by the PACU nurse every half hour. Standardized PCA (patient controlled analgesia) morphine was used to control pain in all patients. A loading dose of up to 0.4 mg/kg was administered as needed to achieve a pain score of less than 3/10. Subsequently, bolus doses of 1.0 mg were self-administered with a lockout interval of 7 minutes. Acetaminophen 325 mg-1.3 g po/pr and naproxen 500 mg po/pr were used as adjunct pain medications. PONV was defined as the presence of feeling nausea or the presence of retching or the presence of vomiting. If PONV was present as defined above, IV Ondansetron 4 mg was initially administered followed by Metoclopramide 10 mg IV if PONV was not relieved and lastly Prochlorperazine 10 mg IV was administered. The patients were monitored in the PACU for 3-4 hr and followed for 24 hr on the gynecological ward.

On the gynecological ward, PONV was defined as in the PACU. For relief of postoperative pain the same PCA protocol was continued on the ward as well as Acetaminophen 325 mg-1.3 g po/pr and Naproxen 500 mg po/pr. For relief of PONV, Dimenhydrinate 25-50 mg IV q4 hr was initially administered as needed and if no relief was obtained then Prochlorperazine 10 mg IV was administered. Only these two medications were approved by our pharmacy on the ward for treatment of PONV.

HRV analysis. Analysis of the raw EKG signal was performed ad-hoc by a research nurse and an anesthesiologist blinded to the patients' PONV status. The raw EKG signal was converted digitally into numerical consecutive R-R intervals. The R-R intervals were then analyzed using two measures of HRV, the Fast-Fourier Transform (FFT) technique and the Wavelet Transform (WT) Technique using MATLAB (Version 6 with Wavelet package; Math Works Inc., Natick Mass.). FFT converts time-domain signals into frequency-domain signals but require that the signals remain stable over time. If existing frequencies within the raw EKG signal change over time, FFT will identify those frequencies but will not resolve where in time those changes occur. The WT technique however, resolves the temporal location of frequency changes and identifies where they occur during the recording.

FFT converts an amplitude vs. time signal (i.e: raw EKG signal) and decomposes it into an amplitude vs. frequency signal. Therefore what was originally a regular pattern of consecutive R-R intervals now becomes a signal with the frequencies of the consecutive R-R intervals. Those predominant frequencies are represented by a power corresponding to the most predominant frequency in the entire signal. For EKG signals, the spectrum is traditionally divided into three regions: the very low frequency range (VLF) 0-0.4 Hz, 0.04 Hz-0.15 Hz the low frequency range (LF) and 0.15-0.4 Hz the high frequency range (HF). In previous tilt-table studies the LF range represents both sympathetic and parasympathetic tone. The HF represents predominantly the parasympathetic tone and the VLF range is non-specific.

The discrete WT technique begins with a "mother" wavelet function, an oscillatory function, which best approximates the characteristic EKG signal to be analyzed. The "Daubechies 4 function" was chosen for this study. This mother function serves as a basis to represent the characteristic frequency of the signal. All other frequencies in the raw biological EKG signal are represented by the mother wavelet function either scaled up or down. This wavelet function, with appropriate scaling, is translated in time to span the entire EKG signal and therefore any changes in frequency can be localized in time which has practical applications. The function is then multiplied by the raw signal to yield a wavelet coefficient which represents the power of correlation between the function and the raw EKG signal. The smallest scaled wavelet coefficient compares the length of two ($2^1$) consecutive measurements (Level 1), which is the highest frequency analyzed. The wavelet function immediately above compares the length of four ($2^2$) consecutive measurements (Level 2), and thus compares half as much length of the signal, and the frequency analyzed is halved compared to the previous wavelet function. In this study, the maximum number of increments forming wavelet coefficient was 5 ($2^5$) or 32 consecutive measurements (Level 5). The variability power is calculated as the sum of the squares of the coefficients for each wavelet function for a given time interval. The Heisenberg Uncertainty Principle implies that the greater the resolution of the frequency signal, the lower will be the resolution of the time signal and vice versa. As a consequence, high frequency signals have poor frequency resolution but good time resolution and low frequency signals have good frequency signals but poor time resolution. The sum of Levels 2, 4 and 8 represent the HF power end of the spectrum analogous to the HF power in the FFT technique. The sum of levels 4 and 5 represent the LF end of the spectrum analogous to the FFT technique.

Statistical analysis. Statistical analysis was performed using GraphPad Instat (Version 3.05, Prism, San Diego, Calif.). The patients were divided into two groups, the nausea group (those who suffered from PONV) and those who did not suffer from nausea (the no-nausea group). The power coefficients using the WT technique were averaged over 2 min, 5 min, 10 min and 20 min intervals were compared using Welch's corrected t-test. The FFT power coefficients were analyzed over the entire 20-min signal and were compared using Welch's corrected t-test. If data passed the Kolmogorov-Smirnov test for normality, a t-test was used for comparison, otherwise, the Mann Whitney test was applied for non-parametric data. All data are presented as mean±SD unless otherwise specified and statistical significance was set as $P<0.05$. The area under the receiver operating curve (ROC) was calculated using MedCalc (MedCalc Software, Belgium).

Results

Demographic data comparing the no nausea group vs the nausea group are shown in Table 2. There was no significant difference in the preoperative risk factors for PONV (smoking status, previous PONV, motion sickness) between both groups. Total intraoperative Fentanyl and total 24 hr Morphine use did not differ between both groups. Total 24 hr Tylenol and Naproxen use did not differ between both groups either.

TABLE 2

Demographic data comparing the no nausea group with the nausea group

|  | No Nausea group (N = 10) Mean ± SD | Nausea group (N = 33) Mean ± SD | P value |
|---|---|---|---|
| Age | 49.2 ± 14.9 | 44.6 ± 10.5 | 0.2838 |
| BMI | 28.7 ± 6.7 | 25.9 ± 5.6 | 0.1975 |
| Preop Haemoglobin | 131.3 ± 17.2 | 128.4 ± 14.1 | 0.5943 |
| Preop Platelets | 310.4 ± 59.0 | 311.1 ± 75.9 | 0.9871 |
| Preop Heart Rate | 85.4 ± 13.3 | 76.6 ± 12.1 | 0.0551 |
| Preop Respiratory Rate | 17.4 ± 3.4 | 16.9 ± 2.3 | 0.6090 |
| Previous PONV | 1/10 (10%) | 7/33 (21%) | 0.6563 |
| Previous motion sickness | 0/10 (0%) | 8/33 (24%) | 0.1653 |
| Current smoking status | 1/10 (10%) | 7/33 (21%) | 0.6563 |
| Diabetes Mellitus | 2/10 (20%) | 1/33 (3%) | 0.1301 |
| Total anesthesia time (min) | 128.9 ± 21.3 | 114.5 ± 26.4 | 0.1227 |
| Total intraoperative crystalloid (mL) | 1070 ± 316.4 | 995.5 ± 254.5 | 0.4475 |
| Total intraoperative blood loss (mL) | 263.0 ± 172.3 | 215.2 ± 169.8 | 0.4409 |
| Total intraoperative midazolam (mg) | 1.8 ± 0.4 | 1.7 ± 0.6 | 0.8005* |
| Total intraoperative propofol (mg) | 204.0 ± 40.7 | 205.2 ± 40.2 | 0.7359* |
| Total intraoperative rocuronium (mL) | 51.0 ± 12.0 | 50.0 ± 12.7 | 0.8000 |
| Total intraoperative fentanyl (µg) | 305.0 ± 55.0 | 310.8 ± 64.4 | 0.8845* |
| Total intraoperative morphine (mg) | 2.8 ± 4.2 | 2.7 ± 4.1 | 0.9067* |
| Highest pain scores PACU (out of 10) | 5.0 ± 2.5 | 6.7 ± 1.6 | 0.0555* |
| Total 24 hr Tylenol (mg) | 1982.5 ± 950.0 | 1674.2 ± 1040.9 | 0.4081 |
| Total 24 hr Naproxen (mg) | 775.0 ± 299.3 | 643.9 ± 472.0 | 0.3165* |
| Total 24 hr Morphine (mg) | 28.6 ± 24.0 | 44.2 ± 24.1 | 0.0787 |
| Mean episodes of nausea in a 24 hr period | 0 |  | N/A |
| Total 24 hr Gravol (mg) | 0 | 50.0 ± 39.5 | N/A |
| Total 24 hr Stemetil (mg) | 0 | 3.3 ± 4.8 | N/A |
| Total 24 hr Ondansetron (mg) | 0 | 2.0 ± 2.5 | N/A |

*All tests were compared using the t-test. None of the variables differed between the two groups.
*These variables did not pass the Kolmogorov-Smirnov test for normality.

In the Fast Fourier Transform (FFT) Technique, the data were analyzed for all patients for 20 min. The groups differed in the very low frequency, low frequency and low frequency/high frequency ratio. In the Wavelet Transform (WT) Technique, HRV was measured at 20 min, 10 min, 5 min and 2 min intervals. The HRV was measured for a total of 20 min. A coefficient was obtained for each time interval. For example for the 20 min interval, one coefficient was obtained for each patient. For the 10 min intervals, two coefficients were obtained (i.e. one for the first ten minutes of the recording and one for the second 10 min of the recording) and the average of the two coefficients is displayed in Table 3. Similar averages are depicted for the 5 min and 2 min intervals. All the low frequency measurements using the WT technique differed between both groups in all time intervals. Only the 2 min time interval differed in the high frequency range. Using ROC curve analysis and the low frequency WT technique for the 20 min intervals, the area under the ROC curve was 0.76 (accuracy), CI=0.606 to 0.877, p=0.0009. This accuracy is superior to other previous studies which used various clinical and subjective criteria in their models.

TABLE 3

HRV analysis

| FFT (Fast Fourier Transform), all 20 min measurements | No Nausea group (N = 10) Mean ± SD | Nausea group (N = 33) Mean ± SD | P value |
|---|---|---|---|
| Total Power | 1334.5 ± 964.7 | 2339.6 ± 1733.4 | 0.1019 |
| Very low frequency | 621.9 ± 465.1 | 1055.1 ± 760.7 | 0.0386 |
| Low frequency | 297.0 ± 249.2 | 690.0 ± 671.7 | 0.0082 |
| High frequency | 381.6 ± 379.6 | 555.9 ± 642.9 | 0.2984 |
| LF/HF ratio | 1.4 ± 1.1 | 2.6 ± 2.6 | 0.0457 |
| WT (Wavelet Transform) |  |  |  |
| Low frequency (20 min) | 379327 ± 264204 | 870466 ± 595178 | 0.0008 |
| Low frequency (10 min) | 191208 ± 130889 | 425116 ± 287177 | 0.0172 |
| Low frequency (5 min) | 95604 ± 65444 | 212558 ± 143589 | 0.0010 |
| Low frequency (2 min) | 33565 ± 19239 | 80423 ± 58271 | 0.0003 |
| High frequency (20 min) | 968357 ± 830672 | 1517638 ± 1323662 | 0.1290 |
| High frequency (10 min) | 430560 ± 412317 | 787982 ± 661253 | 0.1152 |
| High frequency (5 min) | 215280 ± 206158 | 393991 ± 330627 | 0.1152 |
| High frequency (2 min) | 86061 ± 71078 | 151678 ± 130590 | 0.0496 |
| LF/HF (20 min) | 0.5985 ± 0.4198 | 0.9344 ± 0.685 | 0.1489 |
| LF/HF (10 min) | 0.6365 ± 0.3876 | 0.9058 ± 0.6960 | 0.2513 |
| LF/HF (5 min) | 0.6365 ± 0.3876 | 0.9058 ± 0.6960 | 0.2513 |
| LF/HF (2 min) | 0.6238 ± 0.4510 | 0.8393 ± 0.6464 | 0.2489 |

* Comparison of the no nausea group vs the nausea group using the Fast Fourier Transform (FFT) Technique and the Wavelet Transform (WT) Technique.
* All data were compared using the Student's t-test with Welch's correction. All data passed the Kolmogorov-Smirnov test for normality.

While the invention has been described in connection with specific embodiments thereof, it will be understood that it is capable of further modifications and this application is intended to cover any variations, uses, or adaptations of the invention following, in general, the principles of the invention and including such departures from the present disclosures as come within known or customary practice within the art to which the invention pertains and as may be applied to the essential features herein before set forth, and as follows in the scope of the appended claims.

The invention claimed is:

1. A method for determining whether an individual is at risk for post operative nausea and vomiting (PONV), said method comprising:
   a) measuring an autonomic nervous system parameter of said individual preoperatively, wherein the parameter is obtained from an ECG of said individual and is a heart rate variability (HRV) measurement;
   b) deriving a predictive value of risk of PONV based on said measured parameter using an HRV data processor; and
   c) determining if said individual is at risk for PONV.

2. The method as claimed in claim 1 wherein said autonomic system parameter is selected from a measurement of parasympathetic and sympathetic tone.

3. The method as claimed in claim 1 wherein said HRV measurement is based on a frequency of a component of said ECG.

4. The method as claimed in claim 3, wherein said parameter is a measurement of parasympathetic tone and said frequency is a high frequency.

5. The method as claimed in claim 3, wherein said parameter is a measurement of sympathetic tone and said frequency is a low frequency.

6. The method as claimed in claim 3 wherein said frequency is obtained by wavelet transform to generate a wavelet coefficient.

7. The method as claimed in claim 6 wherein said component is selected from R signal, P signal, S signal and T signal.

8. The method as claimed in claim 6 wherein said component is R signal.

9. The method as claimed in claim 6 wherein said parameter is a measurement of parasympathetic tone and said frequency is a high frequency.

10. The method as claimed in claim 6 wherein said parameter is a measurement of sympathetic tone and said frequency is a low frequency.

11. The method as claimed in claim 1, further comprising administering an anti-emetic to said individual.

* * * * *